United States Patent [19]
Kokolus et al.

[11] Patent Number: 6,070,126
[45] Date of Patent: May 30, 2000

[54] IMMUNOBIOLOGICALLY-ACTIVE LINEAR PEPTIDES AND METHOD OF IDENTIFICATION

[75] Inventors: William J. Kokolus, 285 Victoria Blvd., Kenmore, N.Y. 14217; Herbert A. Fritsche; Dennis A. Johnston, both of Houston, Tex.

[73] Assignee: William J. Kokolus, Kenmore, N.Y.

[21] Appl. No.: 09/097,078

[22] Filed: Jun. 12, 1998

Related U.S. Application Data

[60] Provisional application No. 60/049,613, Jun. 13, 1997.
[51] Int. Cl.$^7$ .................................................. C07K 14/00
[52] U.S. Cl. ............................................. 702/19; 530/300
[58] Field of Search ................................. 530/300; 702/19

[56] References Cited

U.S. PATENT DOCUMENTS

| | | | |
|---|---|---|---|
| 4,554,101 | 11/1985 | Hopp | 260/112.5 |
| 5,807,978 | 9/1998 | Kokolus et al. | 530/300 |

OTHER PUBLICATIONS

Abramowitz, M., Stegun, I.,(eds) "Handbook of Mathematical Functions", National Bureau of Standards Applied Mathematics Series, #55, 71–79, 1964.

Atherton et al., "Peptide Synthesis", *Tetrahedron*, 44:843–857, 1988.

Barany et al., Solid–Phase Peptide Synthesis, *The Peptides*, 2: 1–284, 1988.

Fynan et al., "DNA vaccines: Protective immunization by parenteral, mucosal, and gene–gun inoculations", *Proc. Natl. Acad. Sci. USA*, 90:11478–11482, Dec. 1993.

Henttu et al., "cDNA Coding for the Entire Human Prostate Specific Antigen Shows High Homologies to the Human Tissue Kallikrein Genes", *Biochemical and Biophysical Research Communication*, 160: 903–910, 1989.

Hopp et al., "Prediction of protein antigenic determinants from amino acid sequences", *Proc. Natl. Acad. Sci. USA*, 78(6):3824–3828, Jun. 1981.

Kyte et al., "A Simple Method for Displaying the Hydropathic Character of a Protein", *J. Mol. Biol.*, 157:105–132, 1982.

Pellequer et al., "Predicting Location of Continuous Epitopes in Proteins from Their Primary Structure", *Methods in Enzymology*, 203:176–201, 1991.

Robinson, HL, "DNA Vaccines", (Abstract) *Seminars in Immunology*, 9(5) 271, Oct. 1997.

Rosenblum et al., "Amino Acid Sequence Analysis, Gene Construction, Cloning, and Expression of Gelonin, a Toxin Derived from *Gelonium multiflorum*", *J. Interferon and Cytokine Research*, 15:547–555, 1995.

*Primary Examiner*—Karen Cochrane Carlson
*Attorney, Agent, or Firm*—Marianne Fuierer; Howard M. Ellis

[57] ABSTRACT

The present invention relates to identifying protein epitopes and more particularly to a novel method for identifying, determining the location, optimal length of amino acid residues and immunobiological potency of protein epitopes by applying a custom negative cosine function fit algorithm to a protein hydropathy scale. This fit analysis is supplemented with experimental immunobiological data. The amino acid sequence of the protein epitopes of the present invention exhibit a hydrophobic-hydrophilic-hydrophobic hydropathy pattern of an approximately fixed length in a given protein.

8 Claims, 6 Drawing Sheets

Gelonin Kyte-Doolittle hydropathy plot and 15 elisa peptide designations

Designations and rankings for the gelonin immunodominant epitope

IMMUNOBIOLOGICALLY-ACTIVE LINEAR PEPTIDES AND METHOD OF IDENTIFICATION

CROSS REFERENCE TO RELATED APPLICATION

This application claims the benefit of U.S. Provisional Application Ser. No. 60/049,613 filed on Jun. 13, 1997.

TECHNICAL FIELD

The present invention relates to locating protein epitopes and more particularly to a novel method for identifying, determining the location, optimal length of amino acid residues and immunobiological potency of protein epitopes by correlating hydropathy-negative cosine rhythmicity with epitope reactivity.

BACKGROUND OF INVENTION

Epitopes or antigenic determinants of a protein antigen represent the sites that are recognized as binding sites by certain immunoglobulin molecules known as antibodies. While epitopes are defined only in a functional sense i.e. by their ability to bind to antibodies, it is accepted that there is a structural basis for their immunological reactivity.

Epitopes are classified as continuous and discontinuous (Atassi and Smith, 1978, *Immunochemisty*, vol 15 p. 609). Discontinuous epitopes are composed of sequences of amino acids throughout an antigen and rely on the tertiary structure or folding of the protein to bring the sequence together. In contrast, continuous epitopes are short linear peptide fragments of the antigen that are able to bind to antibodies raised against the intact antigen.

Many antigens have been studied as possible serum markers for different types of cancer because the serum concentration of the specific antigen may be an indication of the cancer stage in an untreated person. As such, it would be very advantageous to develop immunological reagents that react with the antigen, and more specifically, with the epitopes of the protein antigen.

To date, methods using physical-chemical scales have attempted to determine the location of probable peptide epitopes which includes looking at the primary structure, that being the amino acid sequence, secondary structure such as turns, helices, and even the folding of the protein in the tertiary structure. Continuous epitopes are structurally less complicated and therefore may be easier to locate, however, the ability to predict the location, length and potency of the site is limited.

Various methods have been used to identify and predict the location of continuous epitopes in proteins by analyzing certain features of their primary structure. For example, parameters such as hydrophilicity, accessibility, and mobility of short segments of polypeptide chains have been correlated with the location of epitopes (see Pellequer et al. 1991, *Method in Enzymology*, vol 203, p. 176–201).

Hydrophilicity, has been used as the basis for determining protein epitopes by analyzing an amino acid sequence in order to find the point of greatest local hydrophilicity as disclosed in U.S. Patent No. 4,554,101. Hopp and Woods (See *Proc. Natl. Acad. Sci. USA*, vol. 78, No. 6, pp. 3824–3828, June 1981) have shown that by assigning each amino acid a relative hydrophilicity numerical value and then averaging local hydrophilicity that the highest local average hydrophilicity value is located in or immediately adjacent to the epitope. However, this method does not provide any information as to the optimal length.

Likewise, the amino acid sequence of a protein as measured by the Kyte-Doolittle (Kyte and Doolittle, 1982, *J. Mol. Biol.* vol. 72, p. 105) scale, is commonly used to evaluate the hydrophilic and hydrophobic tendencies of polypeptide chains by using a hydropathy scale. Each amino acid in the polypeptide chain is assigned a value reflecting its relative hydrophilicity and hydrophobicity which are averaged across a moving section of the sequence. This method offers a graphic visualization of the hydropathic character of the amino acid chain. By using the hydropathic character of the sequence, interior sequence regions which are usually composed of hydrophobic amino acids can be distinguished from hydrophilic exterior sequence regions. This information offers the ability to evaluate the possible secondary structure. However this model, does not predict the optimal length of the epitope or indicate if the effective size of epitopes is unique for each protein molecule.

Accordingly, what is needed is a simple method to identify a peptide epitope and determine the optimal length, location of the epitope within a polypeptide and determine its level of immunopotency.

SUMMARY OF THE INVENTION

In accordance with this invention there is provided a method for identifying immunobiologically-active linear peptide epitopes (hereinafter referred to as Ho-Hi-Ho model epitopes) of a protein antigen characterized by a hydrophobic-hydrophilic-hydrophobic motif, and further, determines the length of amino acid residues and immunopotency of the epitopes.

TERMS

For purposes of this invention, the terms and expressions below, appearing in the specification and claims, are intended to have the following meanings:

"Immunobiological reactivity" as used herein means the ability of a synthetic peptide to react with polyclonal antibodies raised to the whole protein from which the epitope is derived or to a monoclonal antibody raised to a peptide from which the epitope is derived.

"Lagging" as used herein means to move slowly across the entire amino acid residues sequence increasing by one (1) in each step.

"Period number" as used herein means the number of amino acids assigned as the period between −180° to +180° in the negative cosine function plot.

"Fit-Correlation Value" as used herein means a numerical value which is indicative of the fit between the hydropathy plot curve and negative cosine function wherein the value may be positive or negative depending on the fit. The better the fit the more positive the value.

"Ho-Hi-Ho model epitope" as used herein means a peptide having a hydrophobic-hydrophilic-hydrophobic motif which induces an immunogenic response.

"Ho-Hi-Ho model epitope field" as used herein means the optimal length of amino acid residues sequence of a polypeptide containing a reactive site characterized by a hydrophobic-hydrophilic-hydrophobic motif.

"Potential Ho-Hi-Ho model epitope set" as used herein means a set of fit-correlation values for a period assigned to the negative cosine curve.

"Potential Ho-Hi-Ho model epitope" as used herein means the epitopes in each potential Ho-Hi-Ho epitope set.

"Ho-Hi-Ho model theoretical epitope" as used herein means the epitopes in each set that have a positive fit-correlation value indicating a region of hydrophobic-hydrophilic-hydrophobic and which have a theoretical ranking indicating the relative value of the positiveness, that being, the highest positive fit-correlation value is ranked number one.

"Number Range" as used herein means the numerated amino acid sequence number region of the amino acid sequence having a length equal to a period number, i.e. if the period is 10, then the sequence number ranges could be 1–10, 2–11, 3–12 and so on until (n(m−1)) where n is equal to the number of amino acid residues in the entire polypeptide and m is the period number.

"p-value" as used herein means the observed significance level for a statistical test.

A primary object of the present invention is to provide a method for determining Ho-Hi-Ho model epitope fields of proteins.

Another object of the present invention is to identify potential epitopes of a protein molecule by obtaining a fit-correlation measurement between a hydropathy plot representing the hydropathic nature of a protein's amino acid sequence and a negative cosine curve function.

Yet another object of this invention is to provide a method to determine the optimal size of the epitopes by obtaining a correlation between the epitope reactivity of potential epitopes and their hydropathic field.

A further object of this invention is to determine the immunopotency of an epitope and provide a ranking system delineating between dominant and subdominant epitopes.

A still further object is to provide monoclonal and polyclonal antibodies highly specific for the peptide epitopes of the present invention which may be utilized in diagnostic testing procedures to determine the presence of an antigen is serum. Additionally, synthetic peptides having the specific amino acid sequence and length of a peptide epitope may be used in an immunization regime wherein the synthetic peptides are recognized by the body's immune system and induce production of corresponding antibodies.

The foregoing objects are achieved by providing a method for determining an optimal length of contiguous amino acid residues of a Ho-Hi-Ho model epitope within a polypeptide, said Ho-Hi-Ho model epitope characterized by a hydrophobic-hydrophilic-hydrophobic motif, the method comprising the steps of:

a) assigning a window average hydropathy value to each amino acid of the polypeptide;

b) generating a hydropathy plot using the window average hydropathy value of each amino acid;

c) fitting each curve segment of the hydropathy plot to a negative cosine function, wherein a specific period number value of the negative cosine function increases within a predetermined chosen period number range after each sequential lagging through the hydropathy plot thereby providing fit-correlation values for each region of amino acid sequence number ranges of the polypeptide when using the specific period number value;

d) generating a potential Ho-Hi-Ho model epitope set for each specific period number value within the chosen period number range, wherein each potential Ho-Hi-Ho model epitope set contains potential Ho-Hi-Ho model epitopes with the amino acid sequence number ranges that have a positive-fit correlation value;

e) ranking each potential Ho-Hi-Ho model epitope with amino acid sequence number range in the potential Ho-Hi-Ho model epitope set according to positive fit-correlation values wherein the epitope with amino acid sequence number range having highest positive-fit correlation value is ranked number one thereby providing ranked Ho-Hi-Ho model theoretical epitopes for each specific period number value;

f) providing peptides that together span the length of the polypeptide, the peptides having a length from about 15 to about 25 mers;

g) generating experimental data on immunobiologic reactivity of said peptides;

h) ranking experiment peptides according to experimental immunobiologic reactivity thereby providing a peptide experimental ranking value for each peptide;

i) comparing amino acid residue sequences of the experimental peptide with amino acid residue sequences of the ranked Ho-Hi-Ho model theoretical epitopes wherein a positive correlation of amino acid residue sequences provides the basis for assigning the experimental peptide a theoretical ranking dependent upon the ranking of a corresponding Ho-Hi-Ho model theoretical epitope thereby providing a peptide theoretical ranking for each peptide when using a potential Ho-Hi-Ho model epitope set derived from a specific period number value;

j) calculating a correlation coefficient by correlating the peptide experimental ranking to the peptide theoretical ranking for each peptide when using a potential Ho-Hi-Ho model epitope set derived from a specific period number value;

k) determining a statistical p-value of the correlation coefficient;

l) determining the specific period number value having lowest statistical p-value; and m) assigning the optimal length to the Ho-Hi-Ho model theoretical epitope wherein the optimal length is the same value as the specific period number value having the lowest statistical p-value.

The present invention further provides for a Ho-Hi-Ho model epitope of contiguous amino acid residues from a polypeptide wherein the Ho-Hi-Ho model epitope is defined by a motif of two hydrophobic and one hydrophilic regions arranged in the following manner hydrophobic-hydrophilic-hydrophobic and characterized by an approximated −180° to +180° negative cosine hydrophilicity pattern wherein said Ho-Hi-Ho model epitope peptide has an optimal length of amino acid residues from about 3 to about 250.

Further provided is a Ho-Hi-Ho model epitope of contiguous amino acid residues from a polypeptide wherein the Ho-Hi-Ho model epitope is defined by a motif of two hydrophobic and one hydrophilic regions arranged in the following manner hydrophobic-hydrophilic-hydrophobic wherein the Ho-Hi-Ho model epitope has an optimal length of amino acid residues which is determined by the steps of:

a) assigning a average hydropathy value to each amino acid of the polypeptide;

b) generating a hydropathy plot using the average hydropathy value of each amino acid;

c) fitting each curve segment of the hydropathy plot to a negative cosine function, wherein a specific period number value of the negative cosine function increases within a predetermined chosen period number range after each sequential lagging through the hydropathy plot thereby providing fit-correlation values for each region of amino acid sequence number ranges of the polypeptide when using the specific period number value;

d) generating a potential Ho-Hi-Ho model epitope set for each specific period number value within the chosen period number range, wherein each potential Ho-Hi-Ho model epitope set contains potential Ho-Hi-Ho model epitopes with the amino acid sequence number ranges that have a positive-fit correlation value;

e) ranking each potential Ho-Hi-Ho model epitope with amino acid sequence number range in the potential Ho-Hi-Ho model epitope set according to positive fit-correlation values wherein the epitope with amino acid sequence number range having the highest positive-fit correlation value is ranked number one thereby providing ranked Ho-Hi-Ho model theoretical epitopes for each specific period number value;

f) providing peptides spanning the length of the polypeptide, the peptides having a length from about 15 to about 25 mers;

g) generating experimental data on immunobiologic reactivity of said peptides;

h) ranking experiment peptides according to experimental immunobiologic reactivity thereby providing a peptide experimental ranking value for each peptide;

i) comparing amino acid residue sequences of the experimental peptide with amino acid residue sequences of the ranked Ho-Hi-Ho model theoretical epitopes wherein a positive correlation of amino acid residue sequences provides the basis for assigning the experimental peptide a theoretical ranking dependent upon the ranking of the sequence approximating a Ho-Hi-Ho model theoretical epitope thereby providing a peptide theoretical ranking for each peptide when using a potential Ho-Hi-Ho model epitope set derived from a specific period number value;

j) calculating a correlation coefficient by correlating the peptide experimental ranking to the peptide theoretical ranking for each peptide when using a potential Ho-Hi-Ho model epitope set derived from a specific period number value;

k) determining a statistical p-value of said correlation coefficient;

l) determining the specific period number value having lowest statistical p-value; and m) determining an optimal length of a Ho-Hi-Ho model epitope by assigning the specific period number value with the lowest statistical p-value to the Ho-Hi-Ho model epitope.

Also provided is an antisera specific for a Ho-Hi-Ho epitope of contiguous amino acid residues from a polypeptide wherein the Ho-Hi-Ho model epitope is characterized by a hydrophobic-hydrophilic-hydrophobic motif and an approximated −180° to +180° negative cosine hydrophilicity pattern having an optimal length of amino acid residues from about 3 about 250. Additionally, the optimal length may be determined by the method disclosed in the present invention.

There is also provided an antigenic composition comprising a Ho-Hi-Ho epitope of contiguous amino acid residues from a polypeptide wherein the Ho-Hi-Ho model epitope is characterized by a hydrophobic-hydrophilic-hydrophobic motif and an approximated −180° to +180° negative cosine hydrophilicity pattern having an optimal length of amino acid residues from about 3 to about 250.

Additionally, the optimal length may be determined by the method disclosed in the present invention.

Still further provided is a diagnostic testing method comprising the steps of:

(i) providing a sample;

(ii) contacting the sample with antisera specific for a Ho-Hi-Ho epitope of contiguous amino acid residues from a polypeptide wherein the Ho-Hi-Ho model epitope is characterized by a hydrophobic-hydrophilic-hydrophobic motif having an optimal length of amino acid residues from about 3 to about 250; and (iii) detecting binding of the antisera to a polypeptide in the sample.

Also provided is a diagnostic testing method comprising the steps of:

(i) providing an antisera sample (ii) contacting said antisera sample with Ho-Hi-Ho model epitope of claim 20; and (iii) detecting the binding said Ho-Hi-Ho model epitope to said antisera sample.

DETAILED DESCRIPTION OF THE PREFERRED EMBODIMENTS

The present invention is concerned with providing a method for identifying Ho-Hi-Ho model epitopes, the length of continuous amino acid residues of the identified epitopes and their location in a protein antigen.

The method to identify Ho-Hi-Ho model epitopes includes generating average hydropathy values for each amino acid of the protein sequence. These average values may be plotted on a hydropathy plot. The hydropathy values of amino acids can be obtained from any of the methods well known in the art including, but not limited to Kyte-Doolittle tables (Kyte and Doolittle, 1982, *J. Mol. Biol.*, vol 72, p. 105) which are based on solubility of amino acids in water vapors, and Hopp-Woods (Hopp and Woods, 1981, Proc. Natl. Acad. Sci., vol. 78, p. 3824) values which are based on the ability of amino acids to bind to a C18 HPLC column.

Preferably the Kyte-Doolittle measurement scale is used wherein a hydropathy value is assigned to each natural amino acid based on side chain (i) interior-exterior distribution and (ii) water-vapor transfer free energy as determined by water-vapor partition coefficients. The Kyte-Doolittle hydropathy index values include the following:

Isoleucine (9.5), Valine (4.2), Leucine (3.8), Phenylalanine (2.8), Cysteine/cystine (2.5), Methionine (1.9), Alanine (1.8), Glycine (−0.4), Threonine (−0.7), Tryptophan (−0.9), Serine (−0.8), Tyrosine (−1.3), Proline (−1.6), Histidine (−3.2), Glutamic acid (−3.5), Glutamine (−3.5), Aspartic acid (−3.5), Asparagine (−3.5), Lysine (−3.9), Arginine (−4.5).

Figure 1:
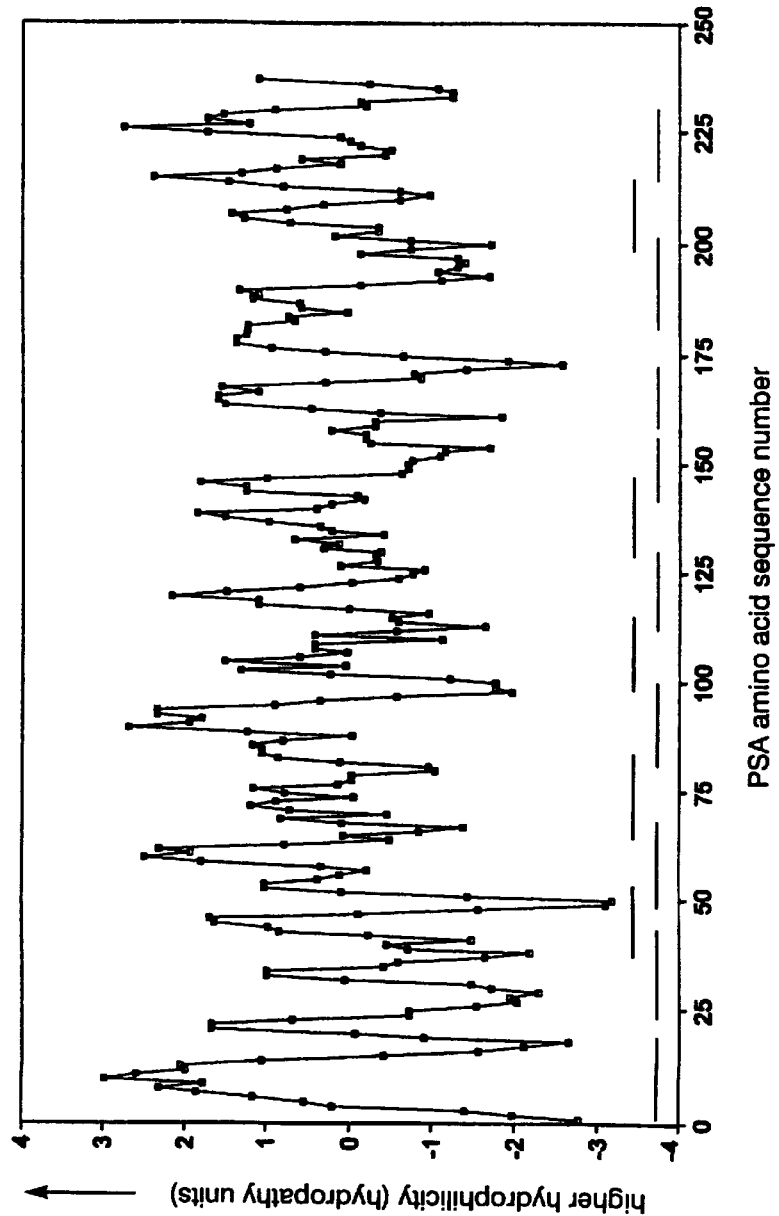
FIG. 1 shows the hydropathy plot for the amino acid sequence of Prostate Specific Antigen PSA.
Figure 2:
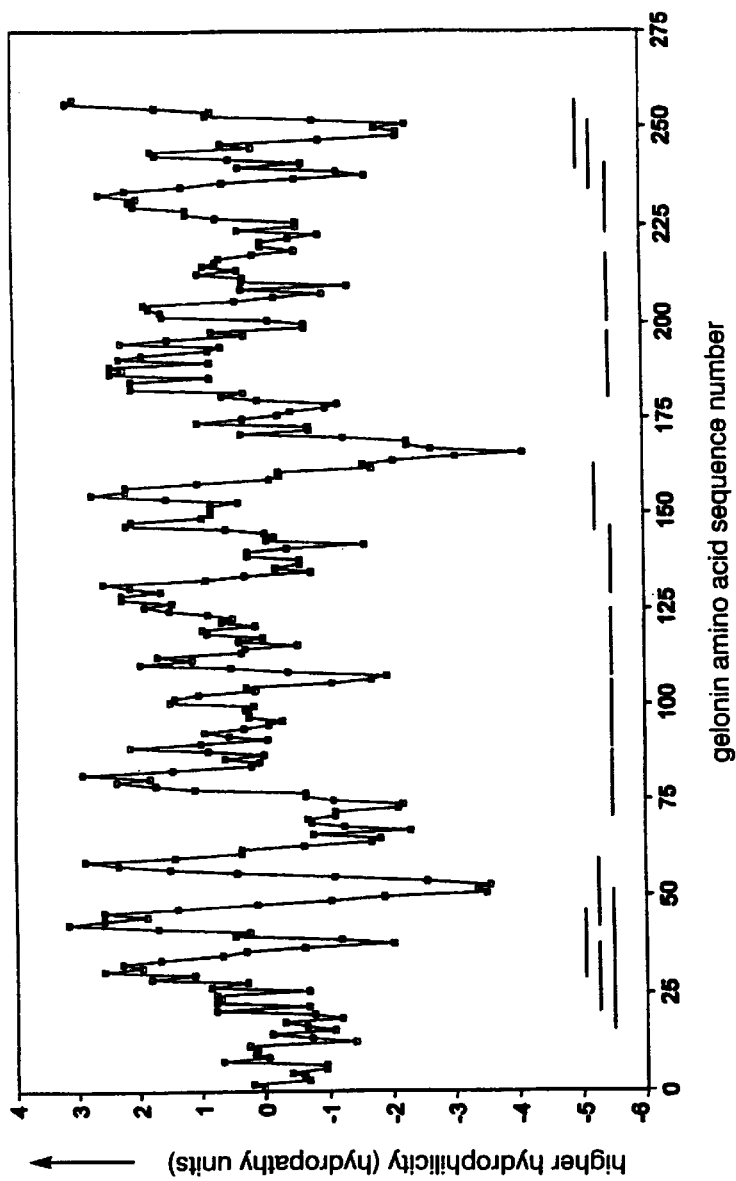
FIG. 2 show the hydropathy plot for the amino acid sequence of Gelonin.

The average hydropathy value of each amino acid is accomplished by averaging the hydropathy values of the amino acid residues within a predetermined window. The window may include any number, however, in a preferred embodiment the length of the window is 5 amino acids. A window average hydropathy value is calculated for each amino acid residue by assigning the average hydropathy value to the amino acid at the center point of each of the moving window segments. Average hydropathy values are obtained by shifting the window by a single amino acid along the entire amino acid sequence of the protein as it advances from the amino to the carboxyl terminus. This is repeated until each amino acid residue is the center point of a window and has been assigned a window average hydropathy value. A plot of these window average hydropathy values is then generated. The plot can be obtained manually, any commercially available or shareware software, or the source code for a custom computer program included in the above-identified reference by Kyte and Doolittle. Preferably, the hydropathy plot is generated by the software package "Wisconsin Package v4" commercially available from Genetics Computer Group, Inc., Madison, Wis. FIG. 1 and FIG. 2 are representative examples of a hydropathy plot for prostate specific antigen (PSA) and gelonin, a plant toxin, respectively.

The resulting hydropathy curve is then fitted to a negative cosine curve function to identify curve regions representing areas having a hydrophobic-hydrophilic-hydrophobic (Ho-Hi-Ho) pattern. The definition of the negative cosine curve is described according to Abramowitz and Stegun, Eds., HANDBOOK OF MATHEMATICAL FUNCTIONS WITH FORMULAS, GRAPHS AND MATHEMATICAL TABLES, National Bureau of Standards and Applied Mathematics, Series #55, June 1964, p. 71–79. Additionally, the specific definition of the negative cosine curve provided in the Microsoft Fortran Library, version 5.1.

Preferably, successive segments of a protein Kyte-Doolittle hydropathy curve are fitted with the negative cosine curve function using custom software with the source code defined in Appendix A. The custom software determines a fit-correlation value for sequential regions of amino acid residues of the protein. The fit-correlation values are dependent upon the period number of the negative cosine curve function which determines the assigned number of amino acids in each region. The assigned number of amino acids in a region is equivalent to the period number used in the negative cosine function. The period number represents the length of amino acid residues in the hydropathy curve region segments that will be analyzed. For each period number specified in the software input, one set (containing of negative cosine function-hydropathy curve region fit-correlation values is generated specific to that period number. The set of fit-correlation values will contain (n(m−1)) values, where n is the number of amino acids in the protein and m is the period number used in the negative cosine curve function.

Specifically, when utilizing the custom software, if $y_l$ is equal to the Kyte-Doolittle hydropathy average value (using a 5-amino acid window as mentioned above) at the amino acid residue or lag point l, where l=1, . . . , n designates the amino acid residue of an amino acid chain containing n amino acids, then $$\lambda_l = \frac{\sum_{k=0}^{m-1}(y_{l+k} - \overline{y}_l) \cdot (c_k - \overline{c})}{\sqrt{(\sum(y_{l+k} - \overline{y}_l)^2) \cdot (\sum(c_k - \overline{c})^2)}}$$

is the hydropathy curve-negative cosine curve function fit-correlation $\lambda$ at lag point l of period number m where $$c_k = -\cos(2\pi k/(m-1))$$

is the negative cosine curve function of period number m, and where $$\overline{c} = \sum_{k=0}^{m-1} c_k/m \quad \text{and} \quad \overline{y}_l = \sum_{k=0}^{m-1} y_{l+k}/m$$

are the respective means.

The fit-correlation is lagged (shifted) over the entire range of amino acids in the protein by increasing the value of l by one (1) until the value (n−(m−1)) is reached. Subsequently, the period number m of the negative cosine curve function is increased by one (1) in order to generate the next potential Ho-Hi-Ho model epitope set. The numerical value for m may be any number greater than 2 extending to the number of amino acid residues in a protein, and preferably, between 8 and 40 thereby creating 33 potential Ho-Hi-Ho model epitope sets. Each epitope set varies slightly in location as the negative cosine function period number used to generate each set is changed; accordingly, the fit-correlation values vary slightly. By changing the period number of the applied negative cosine function, as one would change the aperture of a camera lens, the mathematical perspective of the negative cosine function curve-fit algorithm is altered. This enables the algorithm to detect sequential amino acid hydrophobic-hydrophilic-hydrophobic patterns of a particular length not readily distinguished visually.

Listed in the output of the specifically designed software are the amino acid sequence number ranges that project a hydropathy curve segment having a positive-fit correlation with the negative cosine curve function and are considered the potential Ho-Hi-Ho model epitopes. A positive-fit correlation value indicates the potential presence of a immunobiologically-active linear epitope in the corresponding amino acid sequence number range, i.e. a hydrophobic-hydrophilic-hydrophobic sequence with dominant (high positive-fit correlation) or subdominant (low positive-fit correlation) immunobiological epitope activity. For each period number m, a set of fit-correlation values is generated. For example, if period number m of the negative cosine curve function is chosen from 8 to 40 then there will be 33 different potential Ho-Hi-Ho model epitope sets wherein each set represent a hydropathy curve-negative cosine curve function fit analysis for the entire protein antigen. Each one of these sets has different amino acid sequence number ranges because the period number is changed for each set. For example, the amino acid number ranges for a period number (m) of 10 may include amino acid residues in the number ranges 1–10, 2–11, 3–12, 4–13, and the average hydropathy value of each amino acid in each number range is inputted into the software program until l is equal to (n−(m−1)). Also, the output will give a fit-correlation value for each one of the number ranges such as, 1–10, 2–11, 3–12. More specifically, when using a protein antigen which has 237 amino acid residues in the sequence, l will increase by one until number range 228–237 is inputted into the program. A period number (m) of 11 will include amino acid numbers from 1–11, 2–12, 3–13, 4–14 until l is equal to 227 and number range 227–237 is reached. A set of positive fit-correlation values from each period number m spans the entire protein antigen and provides a potential Ho-Hi-Ho model epitope set.

In each one of the potential Ho-Hi-Ho model epitope sets the amino acid sequence number ranges in the set are theoretically ranked according to the magnitude of the positive-fit correlation values. The sequence number range with the highest correlation value is assigned the number one (1) ranking in each set. This is repeated for each of the sets, that is for each set generated by one of the 33 period numbers utilized in turn by the negative cosine fitting custom software in the range from 8 to 40. The amino acid sequence that corresponds to the amino acid sequence number ranges of the potential Ho-Hi-Ho model epitope set are designated the Ho-Hi-Ho model theoretical epitopes. All sequential amino acid epitopes within a particular potential Ho-Hi-Ho model epitope set are assigned the same length in terms of number of sequential amino acids which is equivalent to the negative cosine function period number utilized to generate that potential Ho-Hi-Ho model epitope set.

To ascertain the locations and the protein specific length of the Ho-Hi-Ho model theoretical epitopes, the optimum negative cosine period number is determined with the aid of experimental data. Experimental data is generated by synthesizing peptides of desired length which together span the entire sequence of the protein antigen. The immunobiologic activity of the individual peptides is tested with antiprotein antibodies.

The peptides can be synthesized using standard methods known to those skilled in the art. In the alternative, a polypeptide may be chemically lysed thereby providing peptides spanning the polypeptide. It may be necessary to thoroughly cover the protein sequence resulting in overlapping of the peptides sequences. While peptides of any length can be used, in a preferred embodiment, the length of the synthesized peptides is from about 10 to about 35 amino acid residues, and more preferably, from about 15 to 25 amino acid residues having sequences that correspond to a portion of a protein.

The term "correspond" as used in the present invention means that an amino acid residue sequence has the same contiguous arrangement of amino acids as that of the protein antigen. However, it is known in the art that substitutions i.e., a conservative substitution for amino acids residues can be made that are immunobiologically equivalent. For instance, substitution for one hydrophobic or polar residue for another at one or many positions in a peptide often does not alter the immunogenic characteristics of the peptide. For example, an aspartic acid residue can be substituted for a glutamic acid, or a leucine for an isoleucine.

Peptides can be synthesized as amides either manually using a Peptide synthesizer and F-moc chemical strategies (Atherton et al., 1988, *Tetradedron*, vol 44, p.19–25) or using automatic peptide synthesizers employing t-BOC chemical strategies (Barany and Merrified, 1988, The Peptides, Analysis, Synthesis, Biology, vol. 2, E. Gross and J. Meienhofer (eds.), Academic Press, New York , p. 1–284). After cleavage from supporting resins, peptides can be purified via gel filtration followed by reverse-phase high-pressure liquid chromatography. The purity of the peptides can be checked by mass spectrometry. With larger peptides, it may be practical to create synthetic genes and express the corresponding protein in a host cell such as, bacterial, insect, yeast or mammalian cell. Genes with nearly any desired nucleotide sequence can be synthesized de novo and inserted into a vector for delivery into a host cell. Transformation of the host cell leads to the synthesis of the protein.

To determine the epitope reactivity of the synthesized peptides, polyclonal antisera to the whole protein may be used. Means of preparing and characterizing antibodies are well known to those skilled in the art and described in *Antibodies: A Laboratory Manual*, Cold Spring Harbor Laboratory, 1988, which reference is incorporated herein by reference. Briefly, polyclonal antibodies are prepared by immunizing an animal with an immunogenic composition comprising the subject protein covalently bonded to a carrier protein such as bovine serum albumin. The immunogenic composition is injected into a host including, but not limited to, rabbits, mice, rats, hamsters, goats, sheep and chicken. In a preferred embodiment, the animal is a rabbit. The levels of antibodies in the serum of the host start to rise in a few days. The early antibodies molecules belong to the immunoglobulin M class (IgM). Approximately ten days after the injection of immunogen, the amount of immunoglobulin M decreases and there is a concurrent increase in the amount of immunoglobulin G (IgG). The level of antibody of the immunoglobulin G class reaches a plateau approximately three weeks after the initial injection. A booster shot of the immunogenic composition produces a further increase in the level of antibodies in the serum. Blood is drawn from the immunized host. The resulting serum, known in the art as antisera, contains the antibodies. Subsequently, the antibodies can be purified and separated from serum proteins by affinity chromatography.

Positive antisera can be identified based on the ability to bind to the protein antigen using any of the variety of methods well know in the art including, but not limited to, radioimmunoassays (RIA), direct and indirect enzyme-linked immunosorbent assay (ELISA), direct, indirect and indirect complement amplified immunofluorescence, immunoblotting, such as Western blotting and also the method of surface plasmon resonance.

Once positive antisera is obtained, it can be used for screening the epitope reactivity of synthesized peptides. Any immunoassay can be used for screening including, but not limited to, ELISA, RIA, surface plasmon resonance, and immunofluorescence. In a preferred embodiment, the immunoassay is ELISA. Briefly, the test peptides are immobilized onto a selected surface exhibiting protein affinity, such as standard microtitre plates. Polyclonal antisera is then added to the wells. Following removal of unbound antisera, the bound antisera is detected by the use of a second antibody conjugated to a detection agent. For example, if the polyclonal antibody is raised in a rabbit, a peroxidase-conjugated goat anti-rabbit IgG can be used as a second antibody. Absorbance can be measured with a microtitre plate reader. Pre-immune and non-immune serum can be used as controls.

ELISA activity values can be calculated by subtracting pre-immune serum absorbency values from immune serum values for each peptide. Each ELISA peptide is given an overall peptide experimental ranking inversely dependent upon the magnitude of its ELISA activity, i.e., the concentration of anti-whole protein antigen polyclonal IgG antibodies that binds to that peptide. This overall peptide experimental ranking may be an average of ELISA activity rankings if more than one assay is performed using ELISA peptide concentrations. If a peptide or group of peptides does not register activity, it will be ranked last. (See Table 1 and 2 in Example 3 for examples of peptide experimental rankings)

Next, a statistical correlation coefficient is obtained between the peptide experimental ranking due to peptide activity and the Ho-Hi-Ho model theoretical epitopes rankings for the same approximate region of the protein. Any statistical method that provides a measure of correlation between ranks may be used in the present invention including, but not limited to the Pearson's rank correlation coefficient, Spearman's rank correlation coefficient and logistic regression analysis.

Each experimental peptide which has been assigned a peptide experimental ranking is also assigned a peptide theoretical ranking. This peptide theoretical ranking corresponds to the Ho-Hi-Ho model theoretical epitope rankings determined by the fit-correlation values using data from the hydropathy-negative cosine curve. The peptide theoretical ranking is determined by comparing the amino acid sequence of an experimental peptide with the Ho-Hi-Ho model theoretical epitopes generated with a specific negative cosine curve function period number. Specifically, if the middle amino acid center point of a Ho-Hi-Ho model theoretical epitope, generated with a specific negative cosine curve function period number is the same as amino acid sequence-wise as any one of the amino acids in an experimentally ranked peptide then the peptide's theoretical ranking is equivalent to the assigned ranking of its corresponding or sequence approximating Ho-Hi-Ho model theoretical epitope. If no Ho-Hi-Ho model theoretical epitope can be aligned with an experimental peptide the experimental peptide is ranked last.

As an example, if using the Spearman's rank correlation coefficient having the formula of:

$$r_s = \frac{SS_{UV}}{\sqrt{SS_{UU}SS_{VV}}}$$

$$\text{where } SS_{UV} = \sum U_i V_i - \frac{(\sum U_i)(\sum V_i)}{n}$$

$$SS_{UU} = \sum V_i^2 - \frac{(\sum V_i)^2}{n}$$

$$SS_{VV} = \sum U_i^2 - \frac{(\sum U_i)^2}{n}$$

having a shortcut formula of:

$$r_s = 1 - \frac{6\sum d_i^2}{n(n^2 - 1)}$$

where $d_i = U_i - V_i$ (difference in the ranks of ith observations for samples 1 ($U_i$) and 2($V_i$) and n=numbers of observation in each sample. The Spearman correlation coefficient for all the peptide's experimental rankings and corresponding peptide theoretical rankings at a specified period number is calculated where $U_i$ is the peptide experimental ranking and $V_i$ is the peptide's theoretical ranking. Preferably, the Spearman correlation coefficients are generated by using commercially available statistical analysis software programs.

The p-value of the correlation coefficient (obtained from standard statistical tables) is plotted against the range of period numbers used in negative cosine curve function. The calculated p-value is known as the Ho-Hi-Ho model strength when using a specific period number. The lowest p-values is selected to represent the optimal Ho-Hi-Ho model epitope of the potential Ho-Hi-Ho model epitope set generated using the optimal period number. In a preferred embodiment, optimal Ho-Hi-Ho model epitopes with p-values less than 0.05 are selected.

By using the method of the present invention, a surprising and unexpected observation was made, namely that the presence of a Ho-Hi-Ho model epitope of a specific length is a distinctive feature of each protein. Furthermore, the size of the optimal Ho-Hi-Ho model epitope is not discernible from the conventional plots of primary, secondary and tertiary protein structure but can be determined by the method of the present invention.

The method of the present invention can be used to select immunobiologically-active linear peptide epitopes from a variety of polypeptides once the amino acid sequence of the polypeptide is determined. Any method know in the art which can determine the amino acid sequence of a protein may be used in the present invention. A preferred method is briefly explained. The first step in the sequence determination of a protein is to cleave the polypeptide chain into smaller peptides and then separate homogeneous samples of these peptides. Trypsin is especially useful for this initial cleavage, because of its specificity for lysine and arginine residues. A polypeptide chain containing five such residues, for example, will be cleaved by trypsin into six shorter peptides. The shorter peptides are separated and analyzed. The amino acid sequence of the isolated peptides is then determined by the sequential cleavage of amino acids from the carboxyl-terminal and amino-terminal ends of each peptide. This can be accomplished by the use of exopeptidases which are specific for the amino- or carboxyl-terminal ends of the peptide chain, or by chemical methods. Carboxypeptidase successively cleaves amino acids from the carboxyl-terminal end of the peptide and it is possible to determine the sequence of the amino acids by following the time course for the release of the amino acids. The most useful chemical method for the analysis of peptide sequences is the reaction of N-terminal amino acids with phenylisothiocyanate. This reaction removes amino acids sequentially from the N-terminal end of the chain as their phenylthiohydantoin (PTH) derivatives. In the first step of the reaction, isothiocyanate undergoes nucleophilic attack by the terminal amino group of the peptide to give a substituted thiourea. This step is carried out in dilute base. Upon treatment with a weak acid, the terminal amino group of the thiourea attacks the peptide bond of the terminal amino acid to give the phenylthiohydantoin derivative of the original N-terminal amino acid. This amino acid may be identified by chromatography and by comparing with standard phenylthiohydantoin derivatives of known amino acids. Cleavage of the peptide bond gives a new N-terminal amino acid that may be identified by repetition of the whole process.

After determining the amino acid sequence of a polypeptide, the method of the present invention may be used to select Ho-Hi-Ho model epitopes from cancer cells, viral, microbial, and other molecules of basic and clinical research interest including, but not limited to examples provided below:

Lymphokines and Interferons:
IL-1, IL-2, IL-3, IL-4, IL-5, IL-6, IL-7, IL-8, IL-9, IL-10, IL-11, IL-12, IFN-α, IFNβ, IFN-γ.

Cluster Differentiation Antigens and MHC Antigens:
CD2, CD3, CD4, CD5, CD8, CD11a, CD11b, CD11c, CD16, CD18, CD21, CD28, CD32, CD34, CD35, CD40, CD44, CD45, CD54, CD56, K2, K1, Pβ, Oα, Mα, Mβ2, Mβ1,LMP1, TAP2, LMP7, TAP1, Oβ, IAβ, IAα, IEβ, IEβ2,IEα, CYP2l, C4B, CYP21P, C4A, Bf, C2, HSP, G7a/b, TNF-α, TNF-β, D, L, Qa, Tla, COL11A2, DPβ2, DPα2, DPβ1, DPα1, DNα, DMα, DMβ, LMP2, TAPi1, LMP7, DOβ, DQβ2, DQα2, DQβ3, DQβ1, DQα1, DRβ, DRα, HSP-70, HLA-B, HLA-C, HLA-X, HLA-E, HLA-J, HLA-A, HLA-H, HLA-G,HLA-F.

Hormones and Growth Factors:

nerve growth factor, somatotropin, somatomedins, parathormone, FSH, LH, EGF, TSH THS-releasing factor, HGH, GRHR, PDGF, IGF-I, IGF-II, TGF-β, GM-CSF, M-CSF, G-CSF1, erythropoietin.

Tumor Markers and Tumor Suppressors:

β-HCG, 4-N-acetylgalactosaminyltransferase, GM2, GD2, GD3, MAGE-1, MAGE-2, MAGE-3, MUC-1, MUC-2, MUC-3, MUC-4, MUC-18, ICAM-1, C-CAM, V-CAM, ELAM, NM23, EGFR, E-cadherin, N-CAM, CEA, DCC, PSA, Her2-neu, UTAA, melanoma antigen p75, K19, HKer 8, pMel 17, tyrosinase related proteins 1 and 2, p97, p53, RB, APC, DCC, NF-1, NF-2, WT-1, MEN-I, MEN-II, BRCA1, VHL, FCC and MCC.

Oncogenes:

ras, myc, neu, raf, erb, src, fms, jun, trk, ret, gsp, hst, bcl and abil.

Complement Cascade Proteins and Receptors:

C1q, C1r, C1s, C4, C2, Factor D, Factor B, properdin, C3, C5, C6, C7, C8, C9, C1Inh, Factor H, C4b-binding protein, DAF, membrane cofactor protein, anaphylatoxin inactivator S protein, HRF, MIRL, CR1, CR2, CR3, CR4, C3a/C4a receptor, C5a receptor.

Viral Antigens:

HIV (gag, pol, qp4l, gp120, vif, tat, rev, nef, vpr, vpu, vpx), HSV (ribonucleotide reductase, α-TIF, ICP4, ICP8, 1CP35, LAT-related proteins, gB, gC, gD, gE, gH, gI, gJ), influenza (hemagluttinin, neuraminidase, PB1, PB2, PA, NP, $M_1$, $M_2$, $NS_1$, $NS_2$), papillomaviruses (E1, E2, E3, E4, E5a, E5b, E6, E7, E8, L1, L2) adenovirus (E1A, E1B, E2, E3, E4, E5, L1, L2, L3, L4, L5), Epstein-Barr Virus (EBNA), Hepatitis B Virus ($gp27^S$, $gp36^S$, $gp42^S$, $p22^c$, pol, x).

Nuclear Matrix Proteins.

The Ho-Hi-Ho model epitopes of the present invention can be used in diagnostic tests, such as immunoassays, to detect viruses, microbes and malignant cells. Immunoassays, in their most simple and direct sense, are binding assays. Certain preferred immunoassays are various types of enzyme linked immunosorbent assays, radioimmunoassays, immunofluorescence and surface plasmon resonance. Immunohistochemical detection using tissue sections is also particularly useful. However, it should be appreciated that detection methods are not limited to such techniques, and Western blotting, dot blotting, FACS analyses, and the like may be used.

After identifying the Ho-Hi-Ho model epitopes and determining the optimal length of amino acid residue sequence, peptides can be synthesized that correspond to the exact amino acid sequence and length of residues. In turn, polyclonal antibodies or monoclonal antibodies can be generated specific for a peptide.

Briefly, monoclonal antibodies are produced by immunizing animals, such as rats or mice with the peptide antigen of choice. Once the animals are making a good antibody response the spleens or lymph node cells are removed and a cell suspension prepared. These cells are fused with a myeloma cell line by the addition of polyethylene glycol (PEG) which promotes membrane fusion. Only a small proportion of the cells fuse successfully. The fusion mixture is then set up in a culture with medium containing "HAT". HAT is a mixture of Hypoxanthine, Aminopterin and Thymidine. Aminopterin is a powerful toxin which blocks a metabolic pathway. This pathway can be bypassed if the cell is provided with the intermediate metabolites hypoxanthine and thymidine. Thus, spleen cells can grow in HAT medium, but the myeloma cells die in HAT medium because they have a metabolic defect and cannot use the bypass pathway. When the culture is set up in the HAT medium it contains spleen cells, myeloma cells and fused cells. The spleen cells die in culture naturally after 1–2 weeks and the myeloma cells are killed by the HAT medium. Only fused cells survive because they have the immortality of the myeloma cells and the metabolic bypass of the spleen cells. Some of the fused cells will have the antibody producing capacity of spleen cells. The wells containing growing cells are tested for production of the desired antibody (often by RIA or ELISA) and, if positive, the cultures are cloned, that is, plated out so that only one cell is in each well. This process produces a clone of cells derived from a single progenitor, which is both immortal and produces monoclonal antibody. These highly specific, monoclonal antibodies may be used as reagents for numerous applications ranging from specific diagnostic tests to "magic bullets" in immunotherapy of different types of cancer. In immunotherapy, various drugs or toxins may be conjugated to the monoclonal antibodies and delivered to the tumor cells against which the antibodies are specific.

The Ho-Hi-Ho model epitopes of the present invention can also be used in prophylactic or therapeutic vaccines to elicit immune responses. Vaccines produced by microorganism such as yeast, through recombinant DNA technology provide another area that may be benefitted by the present invention. The DNA that codes for a Ho-Hi-Ho model epitope can be spliced into the DNA of yeast, which, in turn can produce copies of the peptide. In this regard, production of vaccines against hepatitis B may provide greater quantities of a safer vaccine than the vaccine prepared from blood plasma of humans.

Synthetic vaccine can be prepared by chemically synthesizing a chain of amino acids corresponding to the sequence of amino acids of the Ho-Hi-Ho model epitopes. The amino acid chain containing the Ho-Hi-Ho model epitopes is disposed on a physiologically acceptable carrier and diluted with an acceptable medium. The synthetic vaccines may contain one or a plurality of Ho-Hi-Ho model epitopes of at least one antigen. Vaccines are contemplated for the following antigens, including, but not limited to Hepatitis B surface antigen histocompatibility antigens, influenza hemagglutinin, fowl plague virus hemagglutinin and rag weed allergens Ra3 and Ra5. Also, vaccines are contemplated for the antigens of the following viruses including, but not limited to vaccinia, Epstein Barr virus, polio, rubella, cytomegalovirus, small pox, herpes, simplex types I and II, yellow fever, and many others.

Antigen compositions are contemplated by the present invention which include antibodies specific for peptides with a hydrophobic-hydrophilic-hydrophobic motif having a length of amino acid residues determined by the method of the present invention and which may be administered in the form of injectable, pharmaceutical compositions. A typical composition for such a purpose comprises a pharmaceutically acceptable carrier. For instance, the composition may contain about 10 mg of human serum albumin and from about 20 to 200 micrograms of the labeled monoclonal antibody or fragment thereof per milliliter of phosphate buffer containing NaCl. Other pharmaceutically acceptable carriers include aqueous solution, non-toxic excipients, including salts, preservative, buffers and the like. Examples of non-aqueous solvents are propylene glycol, polyethylene glycol, vegetable oil and injectable organic esters such as ethyloleate. Aqueous carrier include water, alcoholic/aqueous solutions, saline solutions, parenteral vehicles such as sodium chloride, Ringer's dextrose, etc. Intravenous vehicles include fluid and nutrient replenishers. The pH and exact concentration of the various components in the pharmaceutical composition are adjusted according to routine skills in the art.

It is further contemplated that a synthesized chain of nucleotides specific to code for a preferred Ho-Hi-Ho model epitope may be used for immunization compositions. Recently, immunization techniques in which DNA constructs are introduced directly into mammalian tissue in vivo have been developed. Known as DNA vaccines, they use eukaryotic expression vectors to produce immunizing proteins in the vaccinated host. Methods of delivery include intramuscular and intradermal saline injections of DNA or gene gun bombardment of skin with DNA-coated gold beads. Mechanistically, gene gun-delivered DNA initiates responses by transfected or antigen-bearing epidermal Langerhans cells that move in lymph from bombarded skin to the draining lymph nodes. Following intramuscular injections, the functional DNA appears to move as free DNA through blood to the spleen where professional antigen presenting cells initiate responses. These methods are described inter alia in Robinson, Sources in Immunology, 9(5): 271–283, (October 1997) and Fynan et al, Proc. Natl. Acad. Sci. USA,, 90:11478–11482 (1993) and incorporated herein by reference.

In another embodiment of this invention, the method can be used to test the potential antigenicity of a peptide antigen prior to being used to generate bulk antisera for vaccines. The Ho-Hi-Ho model epitope of a test antigen can be compared to its standard Ho-Hi-Ho model epitope (obtained when the antigen was known to generate efficacious vaccine). Any deviations from the standard values may indicate alteration or denaturation of the antigen. This is also applicable not just for peptide antigens but for any protein.

In yet another embodiment of the invention, the method can be used to determine Ho-Hi-Ho model epitopes involved in enzyme-substrate interaction, in protein-protein interaction or to differentiate defective proteins.

The following examples using prostate specific antigen and gelonin as antigenic proteins having immunobiologically active linear epitopes will help to illustrate the present invention.

EXAMPLE 1

Hydropathy Plots for PSA and Gelonin

To generate a hydropathy plot for prostate specific antigen (PSA), hydropathy values according to the method of Kyte and Doolittle, were assigned to each amino acid residue. (See Hentuu and Vihko, 1989, Biochem. Biophys. Res. Comm, vol. 160, p. 903–910 for the amino acid sequence of the protein). The window average hydropathy values were then plotted for the entire amino acid sequence of PSA. The plot was generated with the software package "The Wisconsin Package v4" commercially available from Genetics computer Group, Inc., Madison, Wis. and shown in FIG. 2. Likewise, a similar plot was generated for Gelonin and shown in FIG. 3. (For sequence, see Rosenblum et al, 1995, J. Interferon-Cytokine Res. vol. 15, p. 547).

EXAMPLE 2

Determination of Hydrophobic-Hydrophilic-Hydrophobic Regions

The negative cosine curve function of a specific period number was fitted with custom software using the source code disclosed in Appendix A to successive segments of the PSA and gelonin Kyte-Doolittle hydropathy curve. Each point along the hydropathy curve obtained in Example 1 was fitted to a negative cosine curve function from −180° to +180°. The period number of the negative cosine curve function was changed from 8 to 40 producing a series of 33 potential Ho-Hi-Ho model epitope sets. A fit-correlation value was obtained for each lag point l along the amino acid sequence in each chosen period number m. Number ranges having a positive-fit correlation value represented hydrophobic-hydrophilic-hydrophobic regions in the amino acid sequences. The period number m of the negative cosine curve function represented the size of the hydrophobic-hydrophilic-hydrophobic regions, that being, the number of amino acids in the Ho-Hi-Ho model epitopes.

EXAMPLE 3

Determination of Epitope Reactivity

To determine the epitope reactivity, synthesized peptides that together span the length of the protein antigen and polyclonal antisera to the whole protein were used. The PSA and gelonin synthesized peptides were reacted in an indirect ELISA with a standard dilution of polyclonal sheep anti-PSA and polyclonal rabbit anti-gelonin antibodies, respectively.

Polyclonal Antisera:

Sheep pre-immune serum and polyclonal anti-PSA antiserum were provided by Drs. Barry Blustein and Prakash Tewari of Chiron, Inc. The primary inoculation with PSA was performed with complete Freund's adjuvant (CFA) and secondary injections were performed with incomplete Freund's adjuvant (IFA).

Rabbit pre-immune serum and polyclonal antigelonin antiserum were provided by Brenda Barnett of the University of Texas M.D. Anderson Cancer Center, Department of Veterinary Science, Science Park, Bastrop, Tex. The primary immunogen was 0.3 mg of gelonin (Pierce Chemical Co., Rockford, Ill.) in 0.3 ml of 20 mM PBS, pH 7.2, diluted 1:1 with CFA. A secondary immunization two weeks later was the same but with IFA. The rabbit was inoculated subcutaneously in 10 sites on the back with a maximum of 50 1 CFA or IFA at each site. Five milliliters of pre-immune serum was collected just immediately before the primary immunization, and 5 ml of immune serum was obtained two weeks after the secondary injection.

Indirect ELISA

The epitope reactivity of 14 PSA or 15 gelonin synthesized peptides of approximately equal length (18–20 mers) that together traversed the entire amino acid sequence of the respective protein was determined using the indirect ELISA technique. The 13 PSA 18–20 mers, one PSA 14 mer and 15 gelonin 18 mers used in the indirect ELISAs, shown in FIG. 1 and 2 as regions of amino acid sequences in relation to the hydropathy plots, were provided by the Synthetic Antigen Laboratory, The University of Texas M.D. Anderson Cancer Center, Houston, Tex. They were synthesized with f-moc and t-boc methodology (Atherton and Sheppard, 1989). Their compositions were verified by amino acid analysis, and all peptides were confirmed to be of sufficient purity for ELISA by high-performance liquid chromatography.

Each peptide in either the PSA or gelonin ELISA peptide group was soluble in ELISA peptide coating buffer (0.1 M sodium carbonate, 0.6 M sodium chloride, pH 9.6). Fifty microliters of peptide solution was added to quadruplicate wells of duplicate microtitre plates (EIA-RIA™ 3690, Costar Inc., Kenneybunk, Mass.) for testing both pre-immune and immune sera. Thirteen 18–20 mer PSA peptides and one 14 mer PSA peptide were assayed in the PSA ELISA and fifteen gelonin 18 mers were assayed in the gelonin ELISA. The assays were performed four to five times at varying peptide concentrations to rule out the possibility of a peptide concentration effect on the overall ELISA activity results. The PSA ELISA peptides were assayed at 150 (twice), 450, and 4500 pmol per well. The gelonin ELISA peptides were tested at 450 (three times) and 4500 (twice) pmol per well. In practice, the ELISA activity rankings for each peptide at the various peptide concentration levels did not vary significantly. The cellophane-covered, coating-step microtitre plates were incubated and refrigerated overnight at 4° C. The wells were decanted and washed once with deionized water. Immediately thereafter, each well was blocked by adding 180 µl of 5% non-fat dry milk (Carnation, Nestle' Food Co., Glendale, Calif.) dissolved in 50 mM tris-buffered saline, pH 7.6, 0.05% Tween™-20 (TBS-Tw20). The covered blocking-step plates were incubated in a 37° C. water bath for 1.5 hr, decanted, and washed once with deionized water. Fifty microliters of a working dilution of antiserum (diluted so that the maximum optical density [OD] detected in any well after the indicator step was slightly less than 2.5 OD units) were added to each blocked peptide-coated well. Pre-immune and immune sera were assayed on the duplicate microplates using this same dilution. The covered primary antibody-step microplates were incubated in a 37° C. water bath for 2 hr. The wells were washed six times with TBS-Tw20 and a seventh time with deionized water to rinse off detergent. For secondary antibodies, peroxidase-conjugated goat anti-sheep heavy chain immunoglobulin G (IgG) was used to detect bound sheep pre-immune and anti-PSA IgG in the sheep antiserum, and peroxidase-conjugated goat anti-rabbit heavy chain IgG was used with the rabbit pre-immune and anti-gelonin antisera (The Binding Site, Inc., San Diego, Calif.). Fifty microliters of secondary antibody, diluted 1:3333 in TBS-Tw20 with 2.5% nonfat dry milk, was added to each well. The covered secondary antibody-step microplates were incubated in a 37° C. water bath for 1 hr. The wells were washed as previously described. Fifty microliters of o-phenylenediamine (OPD) indicator substrate solution (0.53 mg/ml of OPD-2HCl, 0.53 mg/ml of urea-$H_2O_2$ and 0.067 M phosphate-citrate buffer, pH 5.0. Sigma Fast tablets, Sigma Chemical Co., St. Louis, Mo. was added to each well. The indicator-step microplates were incubated in the dark at 22° C. for 20 min and the reaction stopped with the addition of 25 1 4N $H_2SO_4$. Absorbencies of the well solutions at 490 nm (620 nm background subtraction) were read with a microplate reader and were compiled (450 Microplate Reader, Microplate Manager/PC, v2.01, BioRad Inc., San Francisco, Calif.).

ELISA activity values were calculated by subtracting pre-immune serum absorbency values from immune serum values for each peptide. Each ELISA peptide was given an overall peptide experimental ranking inversely dependent upon the magnitude of its ELISA activity, i.e., the concentration of anti-whole protein antigen polyclonal IgG antibodies that bound to that peptide. This overall experimental ranking was an average of its ELISA activity rankings in the four or five assays performed at the various ELISA peptide concentrations. If a peptide or peptides did not register ELISA activity, it was ranked last. The overall experimental rankings of the ELISA peptides were placed into an ELISA peptide experimental rank set that had constant values throughout the analyses. The experimental ranking results are shown in Table 1 for PSA and Table 2 for Gelonin.

TABLE 1

| Sequence range | PSA peptide | PSA ELISA Experimental rankings (peptide/well, pmol) | | | |
|---|---|---|---|---|---|
| | | 150 | 150 | 450 | 4500 | overall |
| e105 | 1–20 | 5 | 5 | 3 | 3 | 4 |
| e151 | 24–41 | nd(13)* | 13 | 13 | 14 | 13 |
| e81 | 37–55 | 12 | 10 | 10 | 12 | 11 |
| e107 | 49–68 | 9 | 8 | 9 | 9 | 8 |
| e82 | 65–84 | 11 | 12 | 11 | 11 | 12 |
| e108 | 81–100 | 6 | 6 | 6 | 5 | 6 |
| e83 | 97–115 | 4 | 4 | 5 | 7 | 5 |
| e84 | 111–130 | 3 | 3 | 4 | 4 | 3 |
| h26 | 129–148 | nd(1)* | nd(1)* | 1 | 1 | 1 |
| e85 | 145–158 | 14 | 14 | 14 | 13 | 14 |
| e87 | 160–173 | 7 | 7 | 7 | 6 | 7 |
| e86 | 183–201 | 10 | 11 | 12 | 10 | 10 |
| e110 | 199–218 | 8 | 9 | 8 | 8 | 9 |
| e111 | 218–237 | 2 | 2 | 2 | 2 | 2 |

*n, no data.

TABLE 2

| Gelonin peptide | Sequence range | Gelonin ELISA experimental ranking (peptide/well, pmol) | | | | | |
|---|---|---|---|---|---|---|---|
| | | 450 | 450 | 4500 | 450 | 4500 | overall |
| h56 | 19–36 | nd | nd | nd | 11.5 | 11.5 | 11.5 |
| g38 | 23–40 | 11.5 | 11.5 | 11.5 | nd | nd | 11.5 |
| g41 | 29–46 | 11.5 | 11.5 | 11.5 | nd | nd | 11.5 |
| g33 | 36–53 | 6 | 6 | 6 | 7 | 7 | 7 |
| g39 | 44–61 | 11.5 | 11.5 | 11.5 | nd | nd | 11.5 |
| g37 | 72–89 | 11.5 | 11.5 | 11.5 | nd | nd | 11.5 |
| h58 | 90–107 | nd | nd | nd | 11.5 | 11.5 | 11.5 |
| h59 | 108–125 | nd | nd | nd | 11.5 | 11.5 | 11.5 |
| g43 | 127–144 | 1 | 1 | 1 | 1 | 1 | 1 |
| h60 | 143–160 | nd | nd | nd | 4 | 6 | 5.5 |
| g45 | 181–198 | 3 | 4 | 5 | 3 | 4 | 4 |
| g46 | 200–217 | 11.5 | 11.5 | 11.5 | nd | nd | 11.5 |
| g35 | 223–240 | 4 | 3 | 2 | 5 | 3 | 3 |
| g36 | 235–253 | 2 | 2 | 3 | 2 | 2 | 2 |
| g40 | 240–257 | 5 | 5 | 4 | 6 | 5 | 5.5 | nd, no data

ELISA Peptide Theoretical Ranking

ELISA peptide theoretical rank sets were created in which each ELISA peptide in an experimental rank set was also assigned a peptide theoretical ranking equivalent to the ranking of its corresponding or sequence approximating Ho-Hi-Ho model theoretical epitope in the one of the 33 potential Ho-Hi-Ho model epitope sets that was under consideration. More specifically, if the middle amino acid of a Ho-Hi-Ho model theoretical epitope had the same amino acid protein sequence number as any of the amino acids in an ELISA peptide, the theoretical ranking of that peptide was taken as being equivalent to that of the corresponding Ho-Hi-Ho model theoretical epitope. If an ELISA peptide did not intersect in this manner with any Ho-Hi-Ho model theoretical epitope in a given potential Ho-Hi-Ho model epitope set, it was ranked last. If an ELISA peptide intersected, as indicated above, with the center amino acid sequence number of two or more Ho-Hi-Ho model theoretical epitopes in the potential Ho-Hi-Ho model epitope set being considered, it was assigned the higher epitope ranking. This procedure, carried out individually for both PSA and gelonin using their respective 33 potential Ho-Hi-Ho model epitope sets, resulted in the creation of 33 ELISA peptide theoretical rank sets for each protein.

EXAMPLE 4

Figure 3:
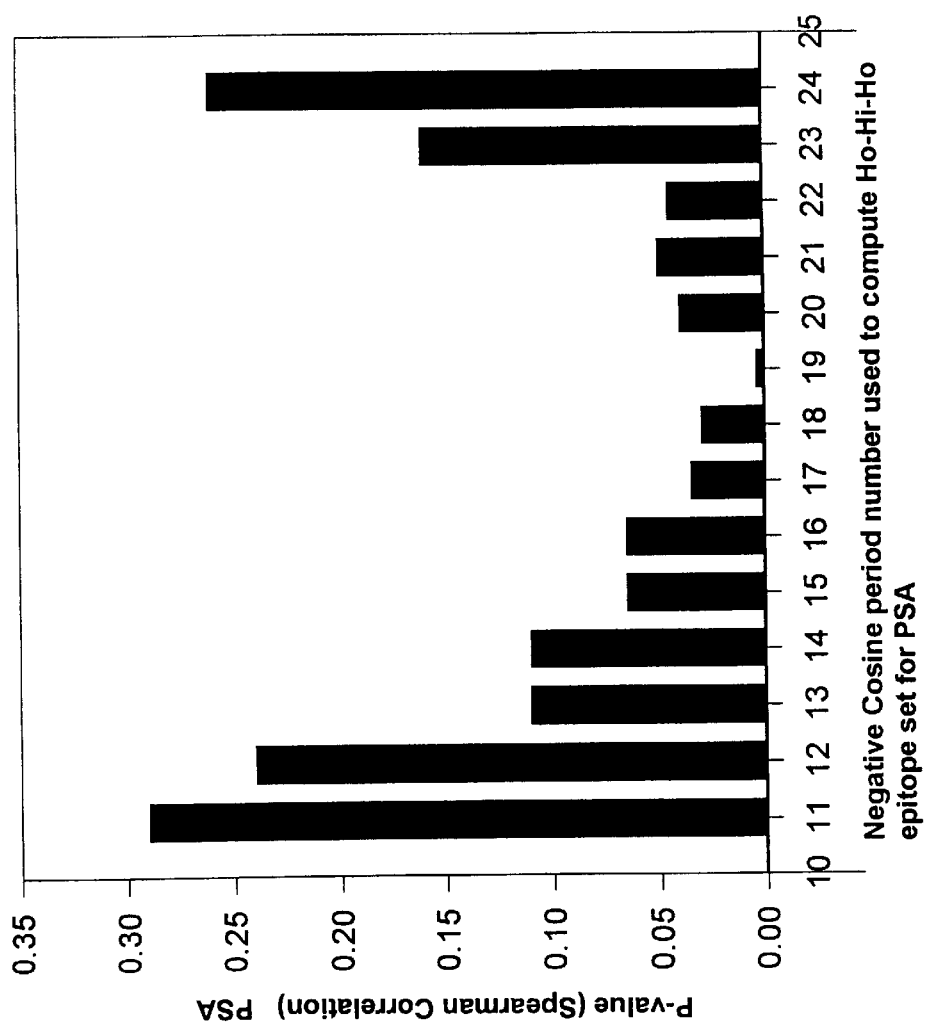
FIG. 3 shows a plot of negative cosine function period number versus Spearman p-value for PSA.
Figure 4:
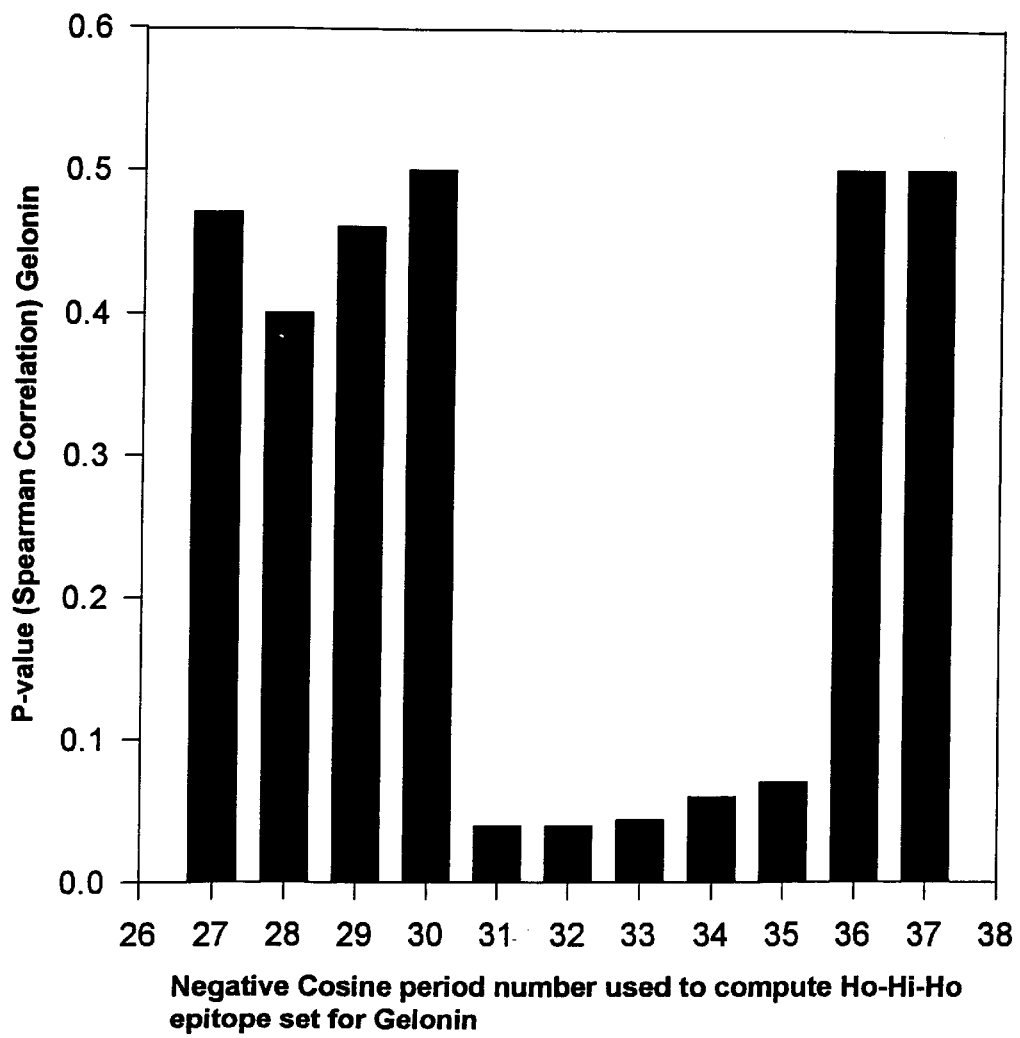
FIG. 4 shows a plot of negative cosine function period number versus Spearman p-value for Gelonin
Figure 5:
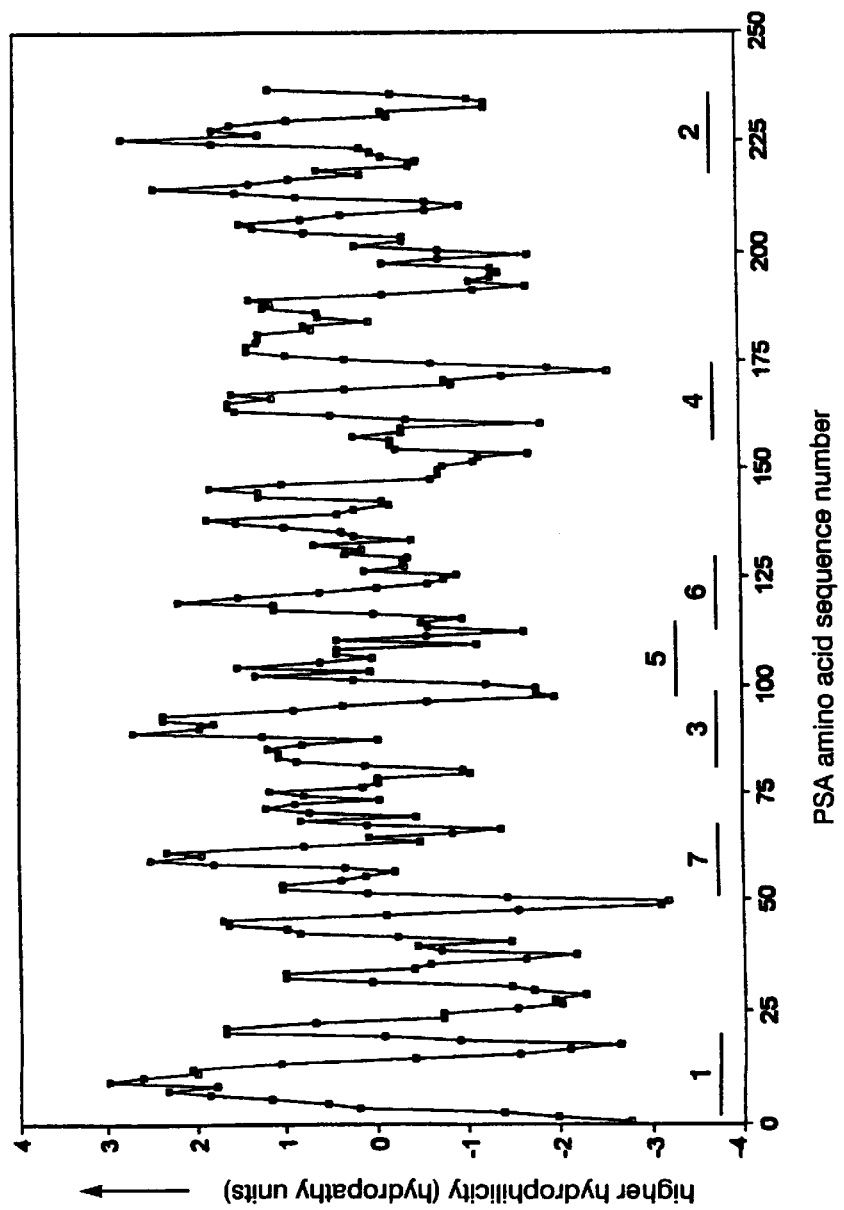
FIG. 5 shows the hydropathy plot for the amino acid sequence of Prostate Specific Antigen (PSA) and further shows the amino acid sequence number ranges for immunodominant Ho-Hi-Ho model epitopes.
Figure 6:
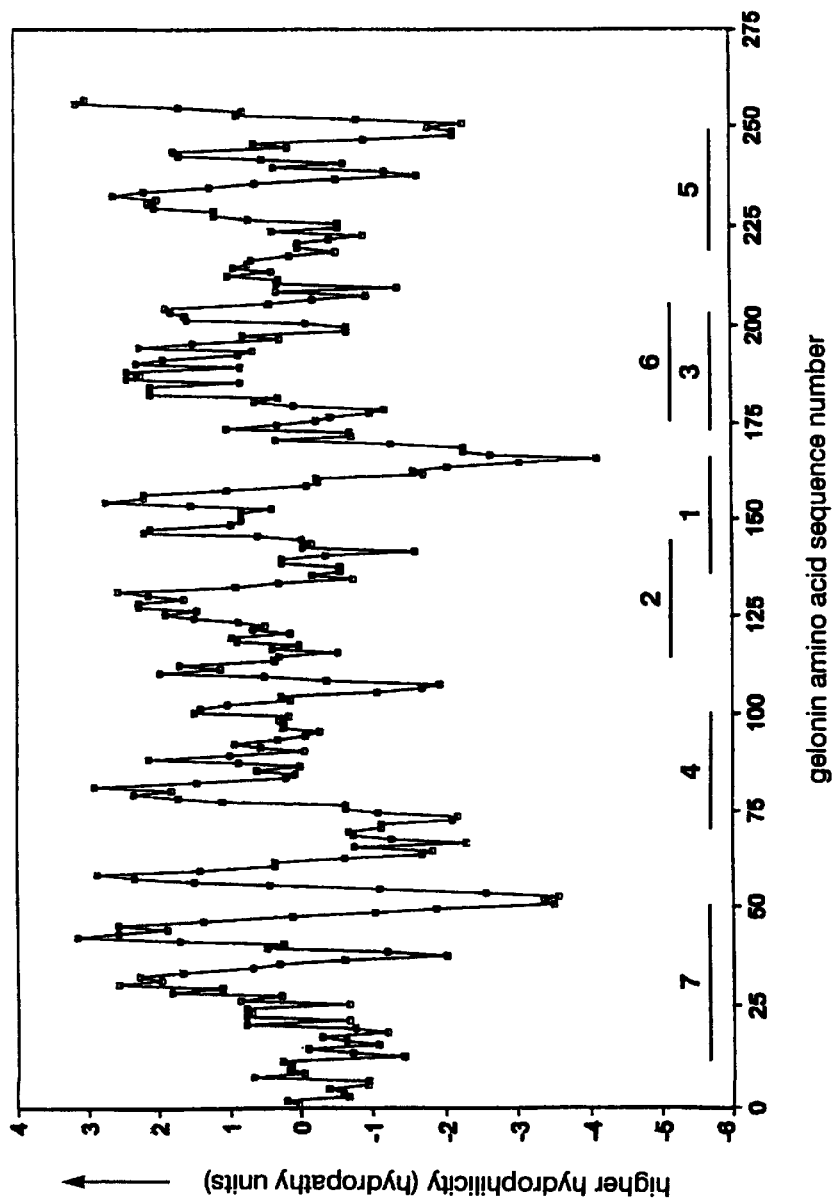
FIG. 6 shows the hydropathy plot for the amino acid sequence of Gelonin and further shows the amino acid sequence number ranges for immunodominant Ho-Hi-Ho model epitopes.

Statistical Correlation Between Peptide Experimental and Theoretical Ranking for Each Period Number To ascertain the optimal length of a Ho-Hi-Ho model theoretical epitope and location in an antigenic protein, the Spearman correlation coefficient p-value was determined for each potential Ho-Hi-Ho model epitope set. One potential Ho-Hi-Ho model epitope set, out of the 33 sets, had a corresponding ELISA peptide theoretical rank set that elicited the most significant Spearman p-value when it ELISA peptide theoretical epitope rankings were correlated with the set of ELISA peptide experimental rankings. This potential Ho-Hi-Ho model epitope set was determined to be the Ho-Hi-Ho model epitope set containing Ho-Hi-Ho model theoretical epitopes and their rankings. The length of the amino acid residue sequence was assigned equivalent to the negative cosine function optimal period number m number. Plotting Spearman's P-value Versus Negative Cosine Period Number FIG. 3 is a plot wherein the Spearman p-values are plotted against the period number m used in the negative cosine curve function. All Spearman correlation p-values below 0.05 formed a trough of statistically significant p-values when the theoretical rank sets of PSA ELISA peptides were derived from the potential Ho-Hi-Ho model epitope sets generated with negative cosine period number m ranging between 17 and 20. The most significant Spearman P-value, 0.005, was elicited by the ELISA peptide theoretical rank set derived from the potential Ho-Hi-Ho model epitope set generated with a negative cosine period number m of 19. The PSA Ho-Hi-Ho model epitopes were assigned an optimal length of 19 amino acids. In Table 3, the Ho-Hi-Ho model fit-correlation rankings based on positive fit-correlation values of the hydropathy regions-negative cosine curve function are shown for period number 19. The PSA immunodominant Ho-Hi-Ho model epitopes, i.e., the seven epitopes ranked highest by using the fit-correlation value ranking were amino acid sequences in number ranges 1–19, 218–236, 81–99, 157–175, 97–115, 112–130, 50–68 and ranked according to this order.

Similarly, as FIG. 4 shows, a trough of significant Spearman p-values were elicited by the ELISA peptide theoretical rank sets derived from the potential Ho-Hi-Ho model epitope sets generated for gelonin using a negative cosine period number m ranging between 31 and 33. The optimal negative cosine period number m was 32 (Spearman P-value 0.038) and contained epitopes 32 amino acids in length. In Table 4, the Ho-Hi-Ho model fit-correlation rankings based on positive fit-correlation values of the hydropathy regions-negative cosine curve function are shown for period number 32. The gelonin immunodominant Ho-Hi-Ho model epitopes having an optimal length of 32 amino acid residues were the amino acid sequences in number ranges of 137–168, 114–145, 172–203, 69–100, 219–250, 175–206, 11–50 and ranked according to order.

TABLE 3

| Amino Acid | Peptide Expt. | PSA Ho-Hi-Ho model Fit-correlation ranking | | | | | |
|---|---|---|---|---|---|---|---|
| numbers | Ranking | Ped No. 12 | Ped No. 15 | Ped No. 16 | Ped No. 19 | Ped No. 22 | Ped No. 23 |
| 1–20 | 5 | 6 | 2 | 1 | 1 | 4 | 7 |
| 24–41 | 13 | 8 | 11 | 11 | 12 | 11.5 | 10.5 |
| 37–55 | 12 | 7 | 5 | 7 | 11 | 11.5 | 10.5 |
| 49–68 | 9 | 4 | 10 | 10 | 7 | 3 | 3 |
| 65–84 | 11 | 14 | 9 | 6 | 8 | 9 | 13 |
| 81–100 | 6 | 9 | 7 | 8 | 3 | 1 | 1 |
| 97–115 | 4 | 10 | 6 | 5 | 5 | 6 | 8 |
| 111–130 | 3 | 1 | 4 | 4 | 6 | 5 | 6 |
| 129–148 | 1 | 11.5 | 12.5 | 12 | 9 | 7 | 5 |
| 145–161 | 14 | 11.5 | 12.5 | 13 | 13 | 13 | 14 |
| 166–173 | 7 | 3 | 3 | 3 | 4 | 2 | 4 |
| 183–201 | 10 | 13 | 14 | 14 | 14 | — | 2 |
| 199–218 | 8 | 2 | 8 | 9 | 10 | 10 | 9 |
| 218–237 | 2 | 5 | 1 | 2 | 2 | 8 | 12 |

TABLE 4

| Amino Acid | Peptide Expt. | Gelonin Ho-Hi-Ho model Fit-correlation ranking | | | | | |
|---|---|---|---|---|---|---|---|
| numbers | Ranking | Ped No. 26 | Ped No. 29 | Ped No. 31 | Ped No. 32 | Ped No. 35 | Ped No. 38 |
| 19–36 | 11.5 | 5 | 5.5 | 7.7 | 7.5 | 10 | 8.5 |
| 23–40 | 11.5 | 5 | 5.5 | 7.5 | 7.5 | 8 | 8.5 |
| 29–46 | 11.5 | 5 | 8.5 | 9.5 | 9.5 | 8 | 8.5 |
| 36–53 | 7 | 9 | 8.5 | 9.5 | 9.5 | 8 | 8.5 |
| 44–61 | 11.5 | 14 | 13 | 13 | 12 | 12 | 11 |
| 72–89 | 11.5 | 7 | 4 | 4 | 4 | 2 | 4 |
| 90–107 | 11.5 | 10 | 11 | 12 | 13 | 13 | 6 |
| 108–125 | 11.5 | 12 | 12 | 14 | 14 | 14 | 2 |
| 127–144 | 1 | 2 | 1 | 2 | 2 | 6 | 14 |
| 143–160 | 5.5 | 3 | 2 | 1 | 1 | 1 | 1 |
| 180–198 | 4 | 1 | 3 | 3 | 3 | 3 | 3 |
| 200–217 | 11.5 | 11 | 10 | 11 | 11 | 11 | 12 |
| 223–246 | 3 | 8 | 7 | 5.5 | 5.5 | 4.5 | 5 |
| 235–252 | 2 | 14 | 14.5 | 5.5 | 5.5 | 4.5 | 14 |
| 240–257 | 5.5 | 14 | 14.5 | 15 | 15 | 15 | 14 |

Immunodominant Ho-Hi-Ho model epitopes were defined as the seven most likely immunobiologically active epitopes in a protein as determined by the using the present invention. See FIGS. 5 and 6. These epitopes had corresponding amino acid sequence number ranges that projected hydropathy curve segments each of which elicited one of the seven largest hydropathy curve segment, negative cosine function fit correlations. The other epitopes in the Ho-Hi-Ho model epitope set were defined subdominant Ho-Hi-Ho model epitopes.

Results

It may be concluded from this example that several sequential amino acid regions in PSA and gelonin adhered strongly to the hydrophobic-hydrophilic-hydrophobic amino acid hydropathy pattern of the protein Ho-Hi-Ho model epitope. This local rhythmic hydropathy pattern enables a protein-specific number of amino acids in the region to act as an immunobiologically active epitope. The epitope length indicated by the optimal negative cosine function period number is specific for PSA (19 amino acids) and for gelonin (32 amino acids). This may indicate that Ho-Hi-Ho model epitopes and their specific length are biochemical entities inherent in a protein. Also, the primary amino acid sequence thus plays a vital role in determining the location, length and immunobiological potency of protein Ho-Hi-Ho model sequential epitopes.

APPENDIX A

FORTRAN PROGRAM FOR FITTING HYDROPATHY PLOT TO NEGATIVE COSINE FUNCTION

We claim:

1. A method for determining an optimal length of contiguous amino acid residues of a Ho-Hi-Ho model epitope within a polypeptide, said Ho-Hi-Ho model epitope characterized by a hydrophobic-hydrophilic-hydrophobic motif, the method comprising the steps of:

a) assigning a window average hydropathy value to each amino acid of the polypeptide;

b) generating a hydropathy plot using said window average hydropathy value of each amino acid;

c) fitting each curve segment of said hydropathy plot to a negative cosine function, wherein a specific period number value of said negative cosine function increases within a predetermined chosen period number range after each sequential lagging through said hydropathy plot thereby providing fit-correlation values for each region of amino acid sequence number ranges of said polypeptide when using said specific period number value;

d) generating a potential Ho-Hi-Ho model epitope set for each specific period number value within said chosen period number range, wherein each potential Ho-Hi-Ho model epitope set contains potential Ho-Hi-Ho model epitopes with said amino acid sequence number ranges that have a positive-fit correlation value;

e) ranking each potential Ho-Hi-Ho model epitope with amino acid sequence number range in said potential Ho-Hi-Ho model epitope set according to positive fit-correlation values wherein said the potential Ho-Hi-Ho model epitope with amino acid sequence number range having highest said positive-fit correlation value is ranked number one thereby providing ranked Ho-Hi-Ho model theoretical epitopes for each specific period number value;

f) providing peptides that together span the length of said polypeptide, the peptides having a length from about 15 to about 25 mers;

g) generating experimental data on immunobiologic reactivity of said peptides;

h) ranking experiment peptides according to experimental immunobiologic reactivity thereby providing a peptide experimental ranking value for each peptide;

i) comparing amino acid residue sequences of said experimental peptide with amino acid residue sequences of said ranked Ho-Hi-Ho model theoretical epitopes wherein a positive correlation of amino acid residue sequences provides the basis for assigning said experimental peptide a theoretical ranking dependent upon the ranking of a corresponding Ho-Hi-Ho model theoretical epitope thereby providing a peptide theoretical ranking for each peptide when using said potential Ho-Hi-Ho model epitope set derived from a specific period number value;

j) calculating a correlation coefficient by correlating said peptide experimental ranking to said peptide theoretical ranking for each peptide when using a potential Ho-Hi-Ho model epitope set derived from a specific period number value;

k) determining a statistical p-value of said correlation coefficient;

l) determining said specific period number value having lowest statistical p-value; and m) determining an optimal length of a Ho-Hi-Ho model epitope by assigning said specific period number value with said lowest statistical p-value to said Ho-Hi-Ho model epitope.

2. The method according to claim 1 wherein said period number range of said negative cosine curve function is from about 8 to about 40.

3. The method according to claim 1 wherein said average hydropathy value is calculated using 5 amino acids residues in each set.

4. The method according to claim 1 wherein said correlation coefficient is calculated using a statistical method that provides a measure of correlation between ranks selected from the group consisting of Pearson's rank correlation coefficient, Spearman's rank correlation coefficient and logistic regression analysis.

5. The method according to claim 1 wherein said experimental data on immunogenic reactivity of said peptides may be generated by a testing method selected from the group consisting ELISA, RIA, surface plasmon resonance, and immunofluorescence.

6. The method according to claim 1 wherein said hydropathy plot is generated using Kyte-Doolittle hydropathy values.

7. The method according to claim 1 wherein said polypeptide contains at least one Ho-Hi-Ho model epitope selected from the group consisting of IL-1, IL-2, IL-3, IL-4, IL-5, IL-6, IL-7, IL-8, IL-9, IL-10, IL-11, IL-12, IFN-α, IFN-β, IFN-65 , CD2, CD3, CD4, CD5, CD8, CD11a, CD11b, CD11c, CD16, CD18, CD21, CD28, CD32, CD34, CD35, CD40, CD44, CD45, CD54, CD56, K2, K1, Pβ, Oα, Mα, Mβ2, Mβ1, LMP1, TAP2, LMP7, TAP1, Oβ, IAβ, IAα, IEβ, IEβ2, IEα, CYP21, C4B, CYP21P, C4A, Bf, C2, HSP, G7a/b, TNF-α, TNF-β, D, L, Qa, Tla, COL11A2, DPβ2, DPα2, DPβ1, DPα1, DNα, DMα, DMβ, LMP2, TAPi1, LMP7, DOβ, DQβ2, DQα2, DQβ3, DQβ1, DQα1, DRβ, DRα, HSP-70, HLA-B, HLA-C, HLA-X, HLA-E, HLA-J, HLA-A, HLA-H, HLA-G, HLA-F, nerve growth factor, somatotropin, somatomedins, parathormone, FSH, LH, EGF, TSH THS-releasing factor, HGH, GRHR, PDGF, IGF-I, IGF-II, TGF-$\beta$, GM-CSF, M-CSF, G-CSF1, erythropoietin, $\beta$-HCG, 4-N-acetylgalactosaminyltransferase, GM2, GD2, GD3, MAGE-1, MAGE-2, MAGE-3, MUC-1, MUC-2, MUC-3, MUC-4, MUC-18, ICAM-1, C-CAM, V-CAM, ELAM, NM23, EGFR, E-cadherin, N-CAM, CEA, DCC, PSA, Her2-neu, UTAA, melanoma antigen p75, K19, HKer 8, pMel 17, tyrosinase related proteins 1 and 2, p97, p53, RB, APC, DCC, NF-1, NF-2, WT-1, MEN-I, MEN-II, BRCA1, VHL, FCC and MCC, ras, myc, neu, raf, erb, src, fms, jun, trk, ret, gsp, hst, bcl and abil, C1q, C1r, C1s, C4, C2, Factor D, Factor B, properdin, C3, C5, C6, C7, C8, C9, C1Inh, Factor H, C4b-binding protein, DAF, membrane cofactor protein, anaphyla-toxin inactivator S protein, HRF, MIRL, CR1, CR2, CR3, CR4, C3a/C4a receptor, C5a receptor, HIV (gag, pol, qp41, gp120, vif, tat, rev, nef, vpr, vpu, vpx), HSV (ribonucleotide reductase, $\alpha$-TIF, ICP4, ICP8, 1CP35, LAT-related proteins, gB, gC, gD, gE, gH, gI, gJ), influenza (hemagluttinin, neuraminidase, PB1, PB2, PA, NP, $M_1$, $M_2$, $NS_1$, $NS_2$), papillomaviruses (E1, E2, E3, E4, E5a, E5b, E6, E7, E8, L1, L2) adenovirus (E1A, E1B, E2, E3, E4, E5, L1, L2, L3, L4, L5), Epstein-Barr Virus (EBNA), Hepatitis B Virus ($gp27^S$, $gp36^S$, $gp42^S$, $p22^c$, pol, x) and Nuclear Matrix Proteins.

8. The method according to claim 1 wherein said p-value is less than 0.05.

* * * * *